United States Patent
Morillo

(10) Patent No.: US 9,211,288 B2
(45) Date of Patent: Dec. 15, 2015

(54) COMPOSITIONS COMPRISING VORTIOXETINE AND DONEPEZIL

(71) Applicant: H. Lundbeck A/S, Valby (DK)

(72) Inventor: Connie Sanchez Morillo, West Milford, NJ (US)

(73) Assignee: H. Lundbeck A/S, Copenhagen-Valby (DK)

( * ) Notice: Subject to any disclaimer, the term of this patent is extended or adjusted under 35 U.S.C. 154(b) by 0 days.

(21) Appl. No.: 14/649,087

(22) PCT Filed: Dec. 12, 2013

(86) PCT No.: PCT/EP2013/076337
§ 371 (c)(1),
(2) Date: Jun. 2, 2015

(87) PCT Pub. No.: WO2014/090929
PCT Pub. Date: Jun. 19, 2014

(65) Prior Publication Data
US 2015/0297585 A1      Oct. 22, 2015

Related U.S. Application Data

(60) Provisional application No. 61/736,799, filed on Dec. 13, 2012.

(51) Int. Cl.
*A61K 31/495* (2006.01)
*A61K 31/445* (2006.01)

(52) U.S. Cl.
CPC ............. *A61K 31/445* (2013.01); *A61K 31/495* (2013.01)

(58) Field of Classification Search
None
See application file for complete search history.

(56) References Cited

U.S. PATENT DOCUMENTS

2008/0032965 A1    2/2008   Hirst

FOREIGN PATENT DOCUMENTS

WO    2009/062517 A1    5/2009

OTHER PUBLICATIONS

International Search Report for PCT/EP2013/076337 mailed Mar. 21, 2014. 5 pages.
Cachard-Chastel et al., "Prucalopride and donepezil act synergistically to reverse scopolamine-induced memory deficit in C57B1/6j mice", Behavioural Brain Research, vol. 187, No. 2, Oct. 18, 2007, pp. 455-461.
Freret et al., "Synergistic effect of acetylcholinesterase inhibition (donepezil) and 5-HT4 receptor activation (RS67333) on object recognition in mice", Behavioural Brain Research, Apr. 21, 2012, vol. 230, No. 1, pp. 304-308.
Adell, "L-AA21004, a multimodal serotonergic agent, for the potential treatment of depression and anxiety", IDRUGS: The Investigational Drugs Journal, Dec. 2010 vol. 13, No. 12. pp. 900-910.
de Bruin et al., "Two novel 5-HT6 receptor antagonists ameliorate scopolamine-induced memory deficits in the object recognition and object location tasks in Wistar rats", Neurobiology of Learning and Memory, vol. 96, No. 2, Sep. 2011. pp. 392-402.
Riverol et al., "Efficacy and Tolerability of a Combination Treatment of Memantine and Donepezil for Alzheimer's Disease" A Literature Review Evidence, European Neurological Journal, vol. 3, No. 1, Jan. 2011, pp. 15-19.
Seltzer, "Donepezil: an update", Expert Opinion on Pharmacotherapy, vol. 8, No. 7, May 2007, pp. 1011-1023.

*Primary Examiner* — Michael Barker
(74) *Attorney, Agent, or Firm* — Fish & Richardson P.C.

(57) ABSTRACT

Pharmaceutical compositions comprising vortioxetine and donepezil are provided and the use of such composition for the treatment of cognitive dysfunctions.

8 Claims, 12 Drawing Sheets

COMPOSITIONS COMPRISING VORTIOXETINE AND DONEPEZIL

CROSS REFERENCE TO RELATED APPLICATIONS

Figure 1A:
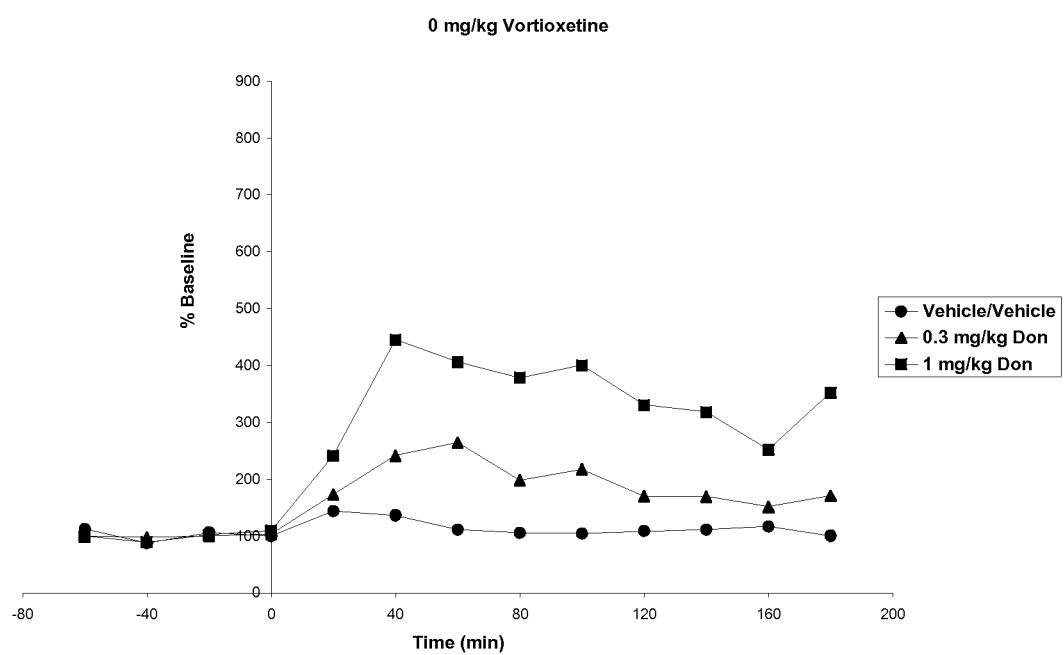

This is a U.S. National Phase application under 35 U.S.C. §371 of International Patent Application No. PCT/EP2013/076337, filed Dec. 12, 2013, which claims the benefit of U.S. Provisional Application No. 61/736,799, filed Dec. 13, 2012, both of which are herein incorporated by reference.

TECHNICAL FIELD

The present invention relates to pharmaceutical compositions comprising vortioxetine and donepezil and to the use of vortioxetine together with donepezil in the treatment of cognitive dysfunction.

BACKGROUND

International patent applications including WO 03/029232 and WO 2007/144005 disclose the compound 1-[2-(2,4-dimethyl-phenylsulfanyl)-phenyl]-piperazine and pharmaceutically acceptable salts thereof. WHO has since published that vortioxetine is the recommended International Non-proprietary Name (INN) for 1-[2-(2,4-dimethyl-phenylsulfanyl)-phenyl]-piperazine. Vortioxetine was formerly referred to in the literature as Lu AA21004. In September 2013 FDA approved vortioxetine for the treatment of major depressive disorder under the trade name Brintellix™.

Vortioxetine is an antagonist on the 5-$HT_3$, 5-$HT_7$ and 5-$HT_{1D}$ receptors, an agonist on the 5-$HT_{1A}$ receptor and a partial agonist on the 5-$HT_{1B}$ receptor and an inhibitor of the serotonin transporter. Additionally, vortioxetine has demonstrated to enhance the levels of the neurotransmitters serotonin, noradrenalin, dopamine, acetylcholine and histamine in specific areas of the brain. All of these activities are considered to be of clinical relevance and potentially involved in the mechanism of action of the compound [*J. Med. Chem.*, 54, 3206-3221, 2011; *Eur. Neuropshycopharmacol.*, 18(suppl 4), S321, 2008; *Eur. Neuropshycopharmacol.*, 21(suppl 4), S407-408, 2011; *Int. J. Psychiatry Clin Pract.* 5, 47, 2012].

Vortioxetine has in clinical trials shown to be a safe and efficacious treatment for depression. A paper reporting the results from a proof-of-concept study to evaluate the efficacy and tolerability of the compound in patients with major depressive disorder (MDD) authored by Alvares et al was made available on-line by *Int. J. Neuropsychopharm.* 18 Jul. 2011. The results from the six weeks, randomised, placebo-controlled study with approximately 100 patients in each arm show that vortioxetine separates significantly from placebo in the treatment of depressive and anxious symptoms in patients with MDD. It is also reported that no clinically relevant changes were seen in the clinical laboratory results, vital signs, weight, or ECG parameters. Results from a long-term study also show that vortioxetine is effective in preventing relapse in patients suffering from MDD [*Eur. Neuropsychopharmacol.* 21(suppl 3), S396-397, 2011]. A study in elderly depressed patients reported in *Int. Clin. Psychopharm.*, 27, 215-227, 2012 shows that vortioxetine may be used to treat cognitive dysfunctions.

The International application published as WO 2009/062517 discloses that vortioxetine may be combined with other types of pharmaceutically active ingredients, such as interferones, opiates, ACE inhibitors and acetylcholine esterase inhibitors.

The impact that serotonin levels and activation or inhibition of serotonin receptors may have on acetylcholine levels has been extensively reviewed—see *Pharmacol Rev*, 59, 360-417, 2007. It emerges from this review that the influence of the serotonergic system on acetylcholine release is extremely complicated and far from understood.

Acetylcholine is a neurotransmitter that acts in the central as well as peripheral nervous system. A low level of acetylcholine has been associated with diseases in which cognitive dysfunction plays a significant role, such as Alzheimer's disease. In fact, administration of acetylcholine esterase inhibitors is one of the two major treatment paradigms for Alzheimer's disease. The other major treatment paradigm is the administration of memantine, an NMDA receptor antagonist. Three acetylcholine esterase inhibitors are presently approved for treatment of Alzheimer's disease, i.e. donepezil, rivastigmine and galantamine. Donepezil was first approved by FDA in 1996; Rivastigmine was first approved by FDA in 2000; and Galantamine was first approved by FDA in 2001.

In addition to the three above mentioned acetylcholine esterase inhibitors, the compound tacrine was previously approved by FDA. Furthermore, the patent literature contains a long range of documents disclosing compounds that act as acetylcholine esterase inhibitors, examples of which include WO 88/08708, WO 93/13100, WO97/38993, WO 2003/082820, U.S. Pat. No. 4,914,102, U.S. Pat. No. 5,231,093, U.S. Pat. No. 5,246,947, EP 268871, EP 298202, EP 409676, EP477903 and EP 703901.

Cognitive dysfunction plays a major role in many CNS (Central Nervous System) diseases. This includes for instance Alzheimer's disease, vascular dementia, and cognitive dysfunction associated with depression, schizophrenia, Parkinson's disease, abuse or Huntington's disease. Cognitive dysfunction is not adequately addressed with current therapy and the present invention seeks to provide alternative and more efficient ways to treat cognitive dysfunction.

SUMMARY OF THE INVENTION

The present inventor has found that the combined use of the acetylcholine esterase inhibitor donepezil and vortioxetine gives rise to a synergistic increase in the extra-cellular level of acetylcholine in the brain.

Accordingly, in one embodiment, the present invention relates to a composition comprising vortioxetine and donepezil.

In one embodiment, the invention relates to the use of vortioxetine and donepezil for the manufacture of a medicament for the treatment of cognitive dysfunction.

In one embodiment, the invention relates to a method for the treatment of cognitive dysfunction, the method comprising the combined administration of vortioxetine and donepezil to a patient in need thereof.

In one embodiment, the invention relates to vortioxetine and donepezil for the combined use in a method for the treatment of cognitive impairment.

FIGURES

Figure 1B:
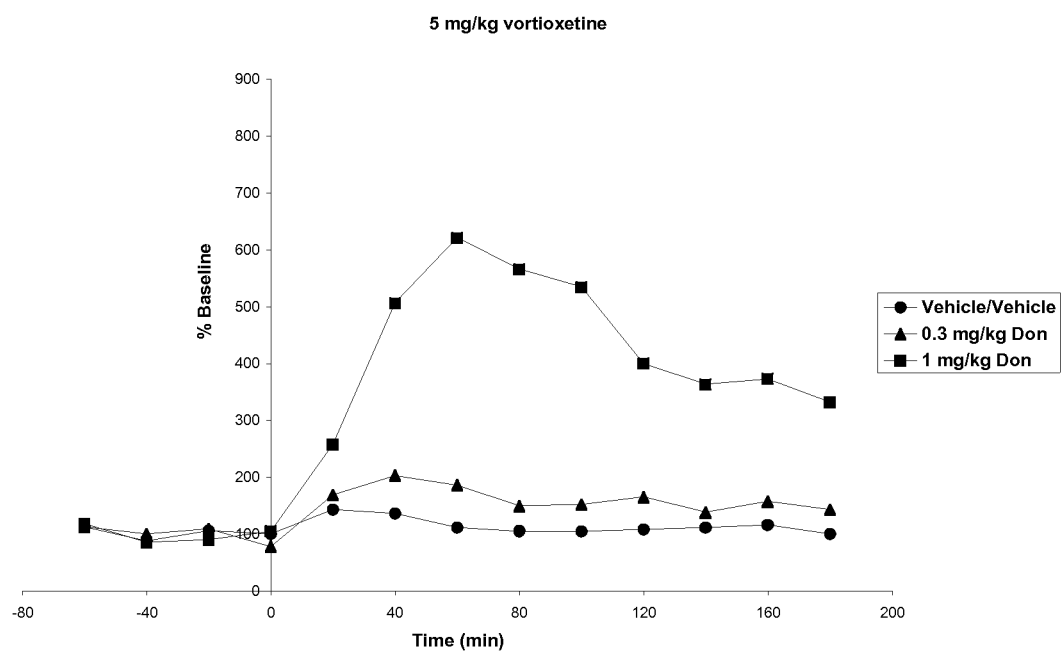
Figure 1C:
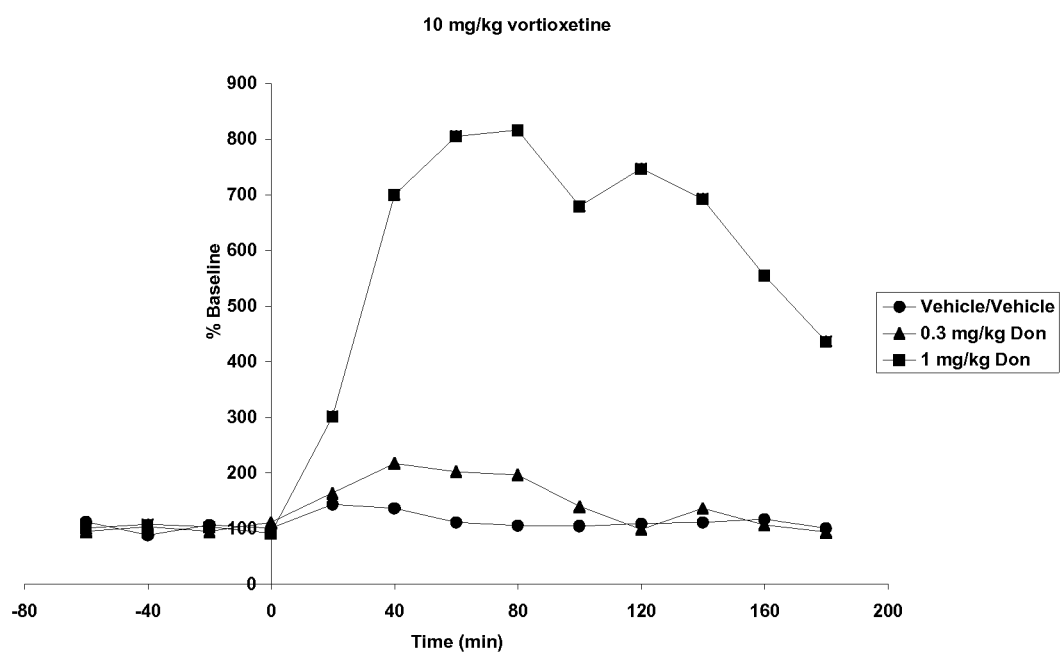

FIG. 1: The pharmacodynamic acetylcholine response in the ventral hippocampus in freely-moving rats after the combined administration of vortioxetine and donepezil. FIG. 1A: Acetylcholine response at 0 mg/kg vortioxetine and 0 mg/kg donepezil (●); 0.3 mg/kg donepezil (▲); or 1 mg/kg donepezil (■). FIG. 1B: Acetylcholine response at 5 mg/kg vortioxetine and 0.3 mg/kg donepezil (▲); and 1 mg/kg donepezil (■). Vehicle/vehicle (●) is included for reference. FIG.

1C: Acetylcholine response at 10 mg/kg vortioxetine and 0.3 mg/kg donepezil (▲); and 1 mg/kg donepezil (■). Vehicle/vehicle (●) is included for reference.

FIG. 2: The pharmacodynamic acetylcholine response in the ventral hippocampus in freely-moving rats after the combined administration of vortioxetine and donepezil.

Figure 2A:
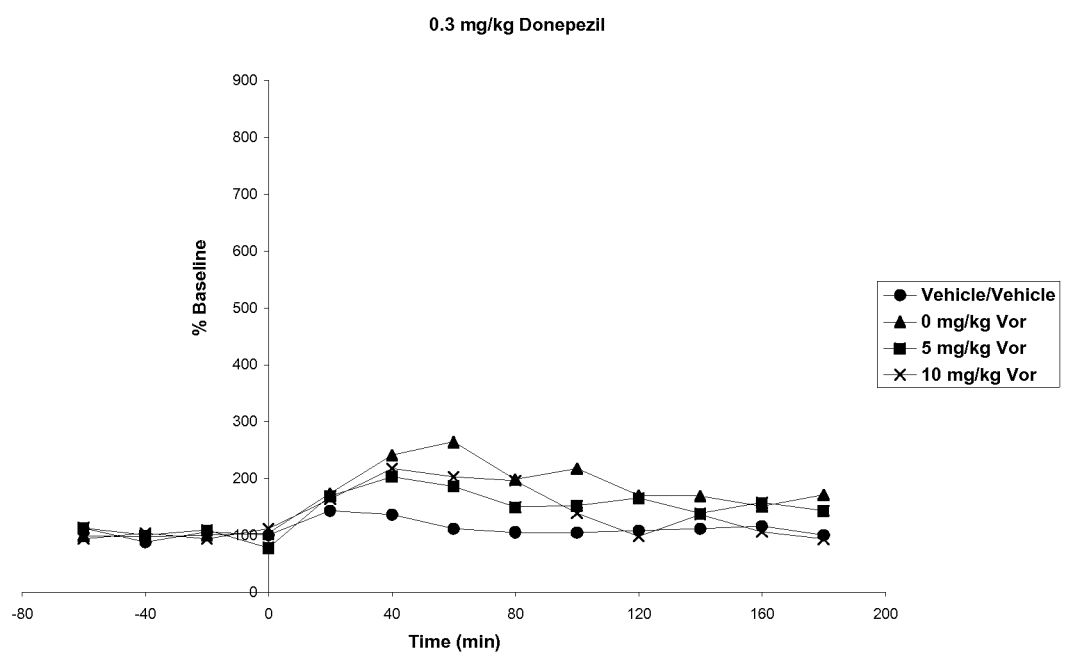
Figure 2B:
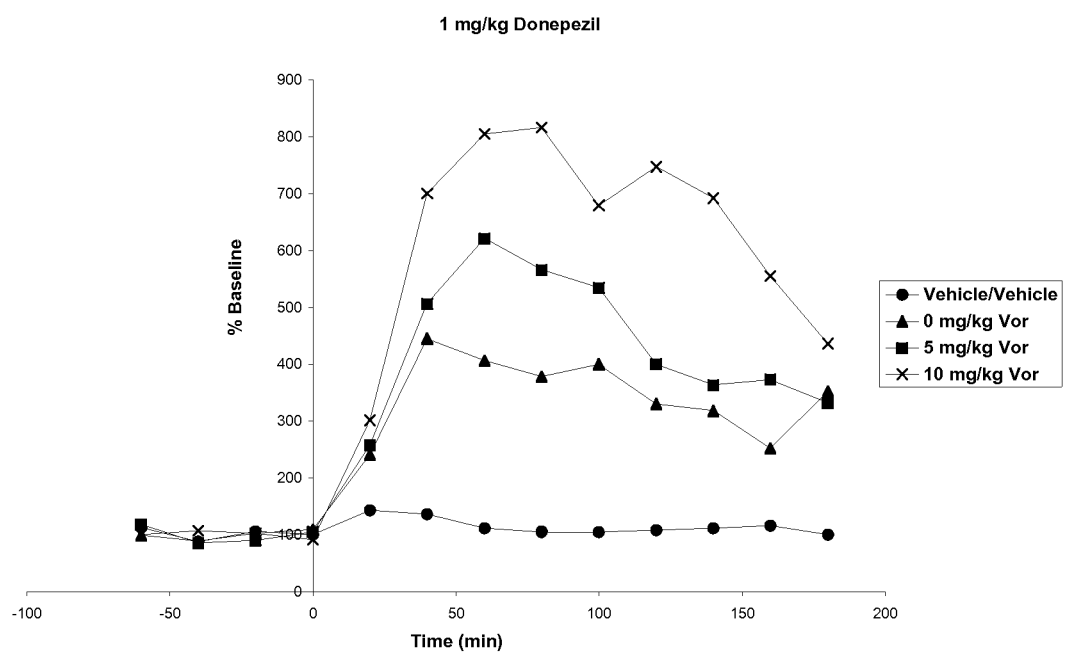

FIG. 2A: Acetylcholine response at 0.3 mg/kg donepezil and 0 mg/kg vortioxetine (▲); 5 mg/kg vortioxetine (■); or 10 mg/kg vortioxetine (X). Vehicle/vehicle (●) is included for reference. FIG. 2B: Acetylcholine response at 1 mg/kg donepezil and 0 mg/kg vortioxetine (▲); 5 mg/kg vortioxetine (■); or 10 mg/kg vortioxetine (X). Vehicle/vehicle (●) is included for reference.

Figure 3:
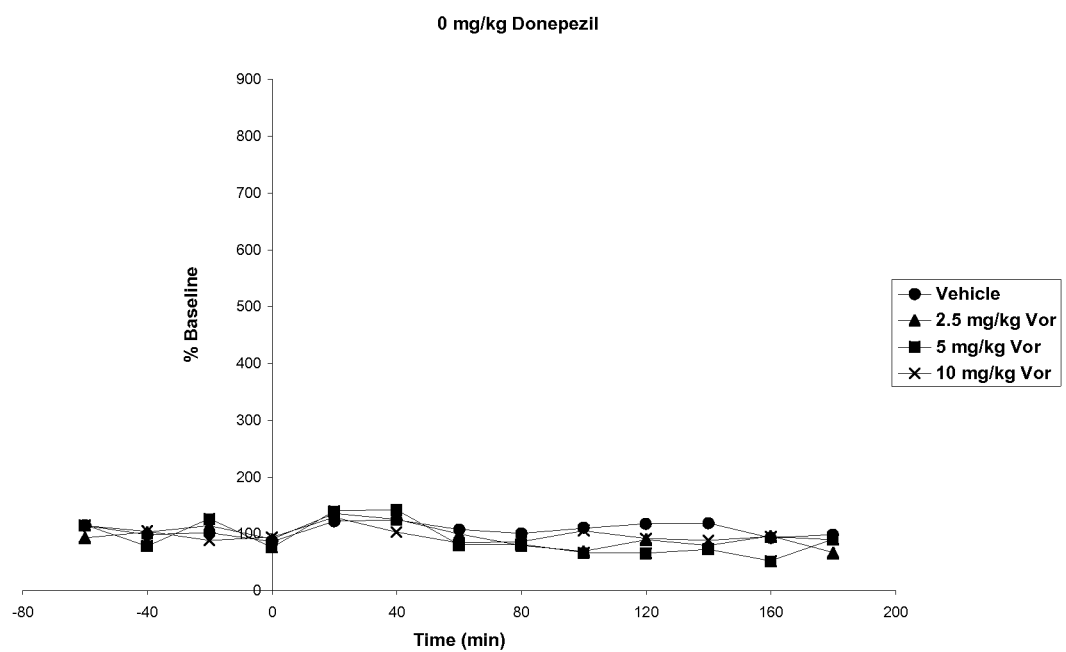

FIG. 3: The pharmacodynamic acetylcholine response in the ventral hippocampus in freely-moving rats after the administration of vortioxetine. Acetylcholine response at 0 (●), 2.5 mg/kg (▲), 5 mg/kg (●) and 10 mg/kg (X) vortioxetine.

Figure 4A:
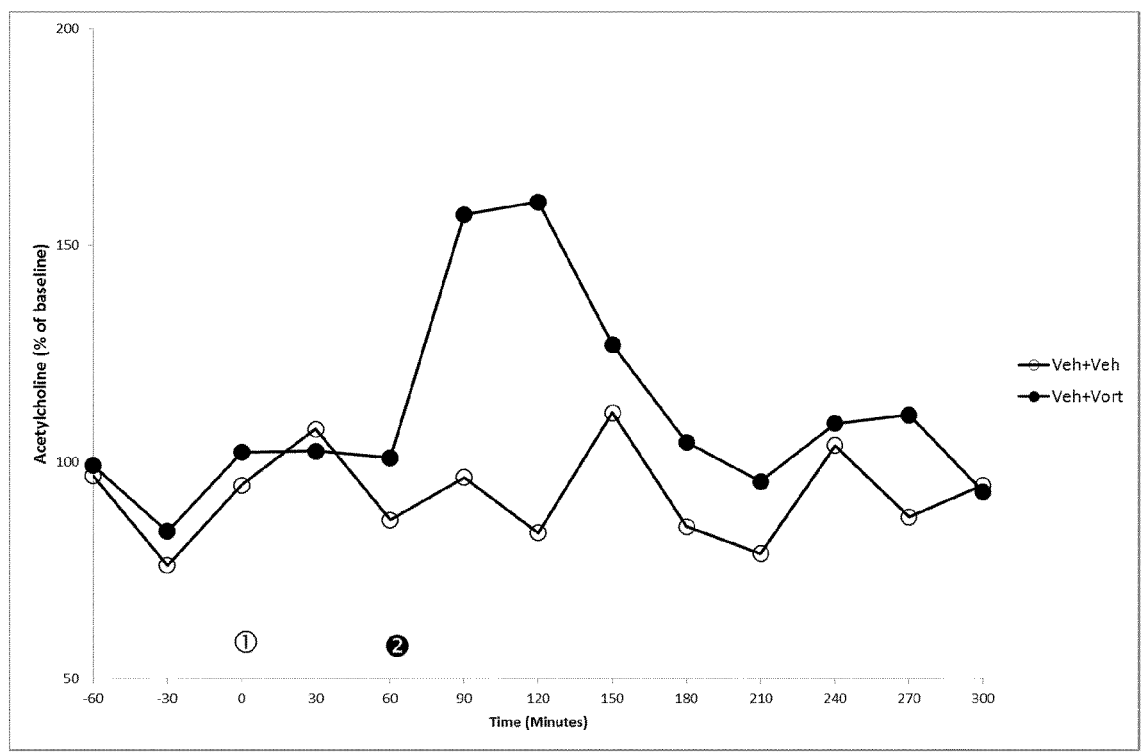
Figure 4B:
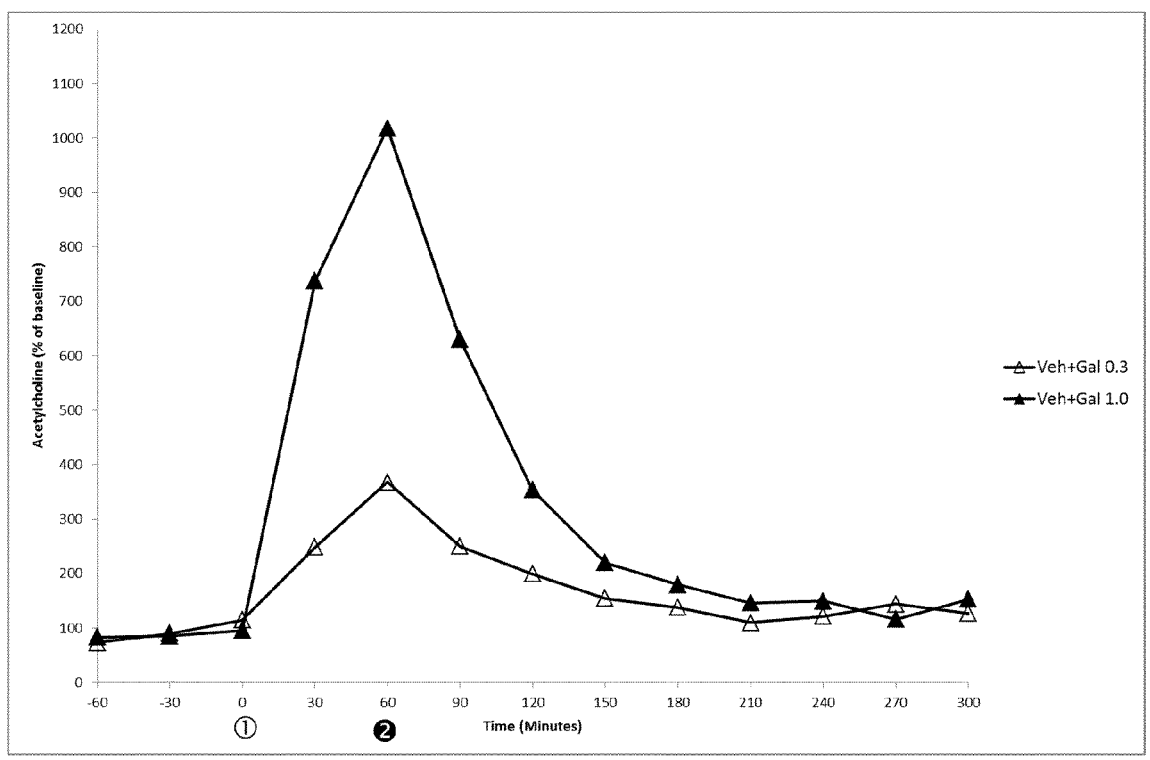
Figure 4C:
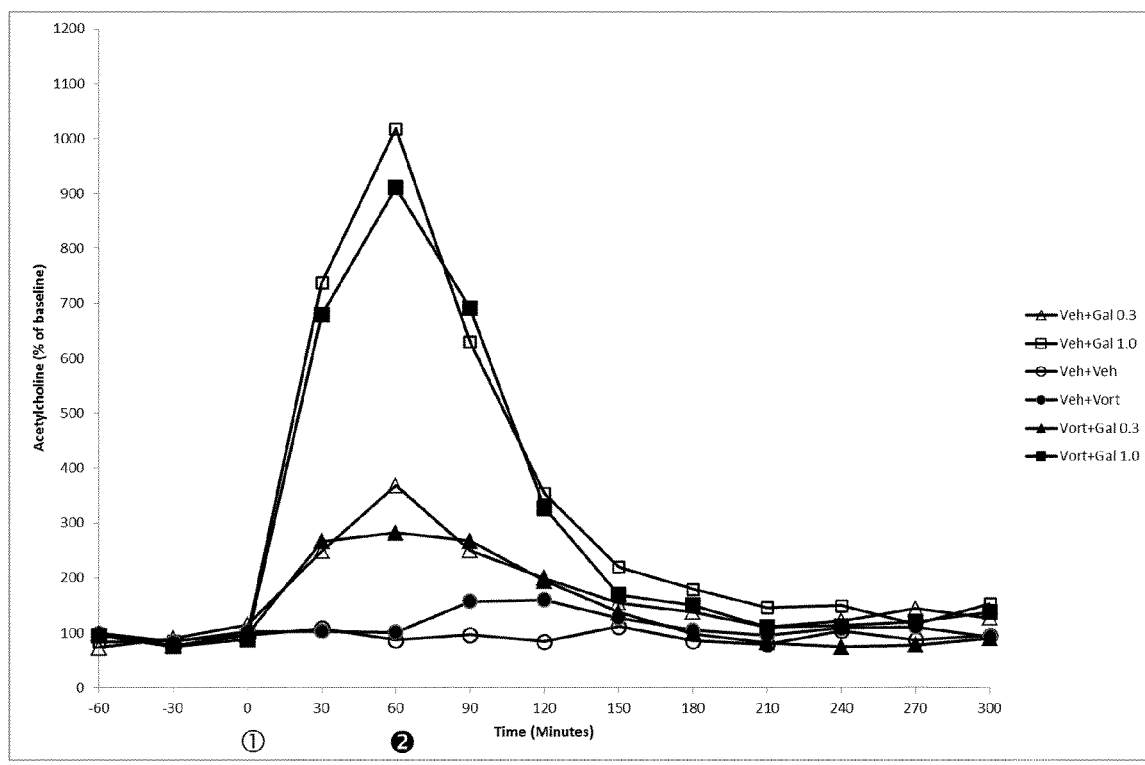

FIG. 4: The pharmacodynamic acetylcholine response in the ventral hippocampus in freely-moving rats after the combined administration of vortioxetine and galantamine. FIG. 4a: Acetylcholine response at vehicle (injected at ①) and vehicle (injected at ❷) (○); and vehicle (injected at ①) and vortioxetine at 10 mg/kg (injected at ❷) (●). FIG. 4b: Acetylcholine response at galantamine at 0.3 mg/kg (injected at ①) and vehicle (injected at ❷) (Δ); and galantamine at 1.0 mg/kg (injected at ①) and vehicle (injected at ❷) (▲). FIG. 4C: Acetylcholine response at vehicle (injected at ①) and vehicle (injected at ❷) (○); vehicle (injected at ①) and vortioxetine at 10 mg/kg (injected at ❷) (●); galantamine at 0.3 mg/kg (injected at ①) and vehicle (injected at ❷) (Δ); galantamine at 1.0 mg/kg ((injected at ①) and vehicle (injected at ❷) (□); galantamine at 0.3 mg/kg (injected at ①) and vortioxetine at 10 mg/kg (injected at ❷) (▲); and galantamine at 1.0 mg/kg (injected at ①) and vortioxetine at 10 mg/kg (injected at ❷) (■).

Figure 5A:
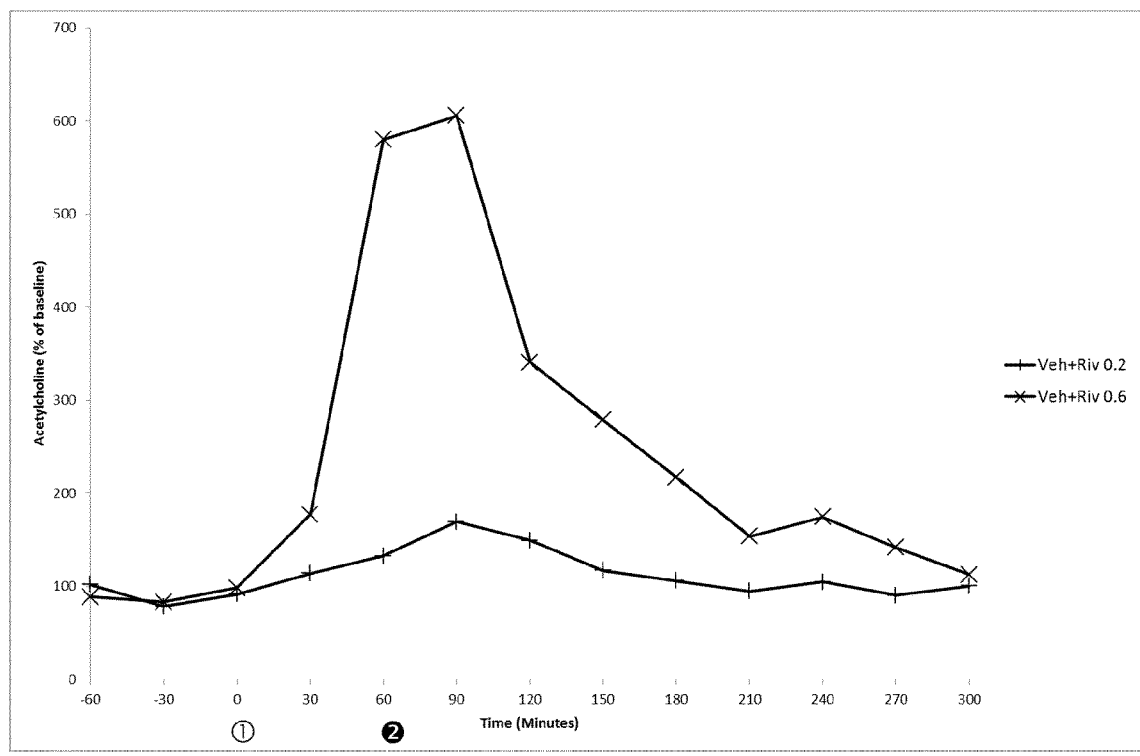
Figure 5B:
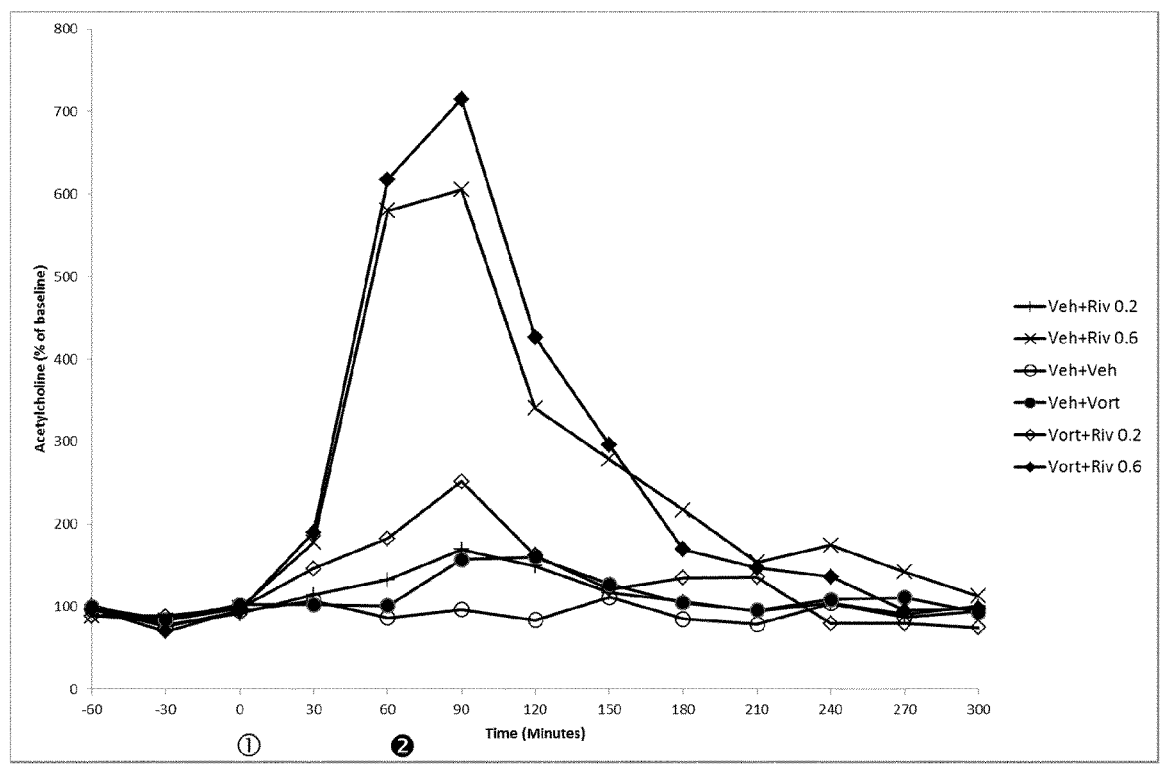

FIG. 5: The pharmacodynamic acetylcholine response in the ventral hippocampus in freely-moving rats after the combined administration of vortioxetine and rivastigmine. FIG. 5a: Acetylcholine response at rivastigmine at 0.2 mg/kg (injected at ①) and vehicle (injected at ❷) (+); and rivastigmine at 0.6 mg/kg (injected at ①) and vehicle (injected at ❷) (x). FIG. 5b: Acetylcholine response at vehicle (injected at ①) and vehicle (injected at ❷) (○); vehicle (injected at ①) and vortioxetine at 10 mg/kg (injected at ❷) (●); rivastigmine at 0.2 mg/kg (injected at ①) and vehicle (injected at ❷) (+); rivastigmine at 0.6 mg/kg ((injected at ①) and vehicle (injected at ❷) (x); rivastigmine at 0.2 mg/kg (injected at ①) and vortioxetine at 10 mg/kg (injected at ❷) (◇); and rivastigmine at 0.6 mg/kg (injected at ①) and vortioxetine at 10 mg/kg (injected at ❷) (◆).

Figure 6:
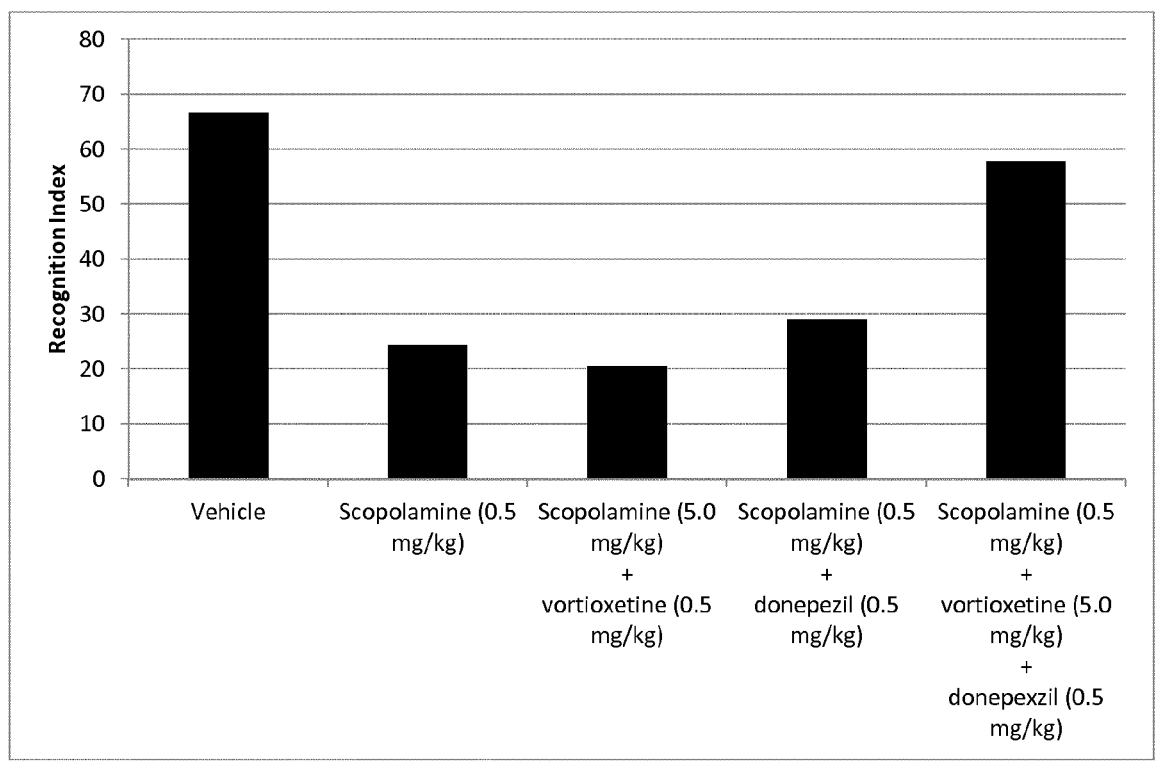

FIG. 6: Recognition Index obtained from novel object recognition in rats treated with vehicle; scopolamine (0.5 mg/kg); scopolamine (0.5 mg/kg)+vortioxetine (5 mg/kg); scopolamine (0.5 mg/kg)+donepezil (0.5 mg/kg); or scopolamine (0.5 mg/kg)+vortioxetine (5 mg/kg)+donepezil (0.5 mg/kg).

DETAILED DESCRIPTION OF THE INVENTION

The present invention encompasses the use of vortioxetine for the treatment of cognitive dysfunction. In the present context, "vortioxetine" includes vortioxetine as the free base and as a pharmaceutically acceptable salt. Particular mention is made of the HBr salt, the tartrate salt and the (DL)-lactate salt.

The molecular structure of vortioxetine free base is depicted below

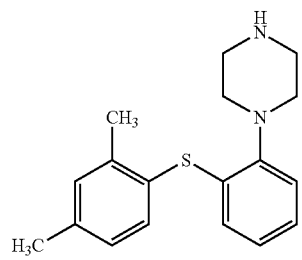 [SMILES: Cc1ccc(Sc2ccccc2N2CCNCC2)c(C)c1]

The present invention encompasses the use of donepezil for the treatment of cognitive dysfunction. In the present context, "donepezil" includes donepezil as the free base and as a pharmaceutically acceptable salt. Particular mention is made of the HCl salt.

The molecular structure of donepezil free base is depicted below.

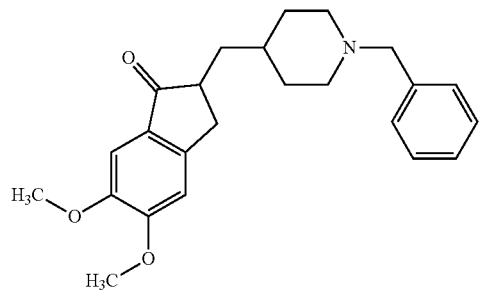 [SMILES: COc1cc2c(cc1OC)C(=O)C(CC1CCN(Cc3ccccc3)CC1)C2]

In more general terms, said pharmaceutically acceptable salts are acid addition salts of acids that are non-toxic. Said salts include salts made from organic acids, such as maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, theophylline acetic acids, as well as the 8-halotheophyllines, for example 8-bromotheophylline. Said salts may also be made from inorganic acids, such as hydrochloric, hydrobromic, sulfuric, sulfamic, phosphoric and nitric acids.

Processes for the manufacture of vortioxetine are disclosed in the International patent applications published as WO 03/029232, WO 2007/144005 and WO 2010/094285. Donepezil is readily available from many commercial suppliers.

The combined administration of vortioxetine and donepezil may take the form of simultaneous administration. In this embodiment, vortioxetine and donepezil are administered to the patient essentially at the same time, either in the form of an administration form that comprises both vortioxetine and donepezil, or in the form of separate administration forms, i.e. a first administration form comprising vortioxetine and a second administration form comprising donepezil.

Alternatively, the combined administration of vortioxetine and donepezil comprises a time gab between the administration of vortioxetine and the administration of donepezil. In this embodiment, either vortioxetine or donepezil may be administered first. As evidenced by the data shown in the Examples part there is a synergistic effect between vortioxetine and donepezil. Said synergistic effect is dependent on the presence of pharmacologically relevant amounts of both vortioxetine and donepezil in the body at the same time. This puts an upper limit to the time gap which may be between the administration of vortioxetine and the administration of donepezil. In practice, the synergistic effect is likely to decline if the administration of vortioxetine and the administration of donepezil is interspaced by more than approximately 2 half-lifes of the first of the two compounds to be administered. In one embodiment, the administration of the two compounds is interspaced by 0-1 half-life of the first compound to be administered. In the present context, "half-life" is the time required for the plasma level of a pharmaceutically active ingredient to reach 50% of its initial value.

The half-life of donepezil in humans is approximately 70 hours [xPharm: The Comprehensive Pharmacology Reference, 1-5, Elsevier, 2007].

The half-life of vortioxetine in humans is approximately 57 hours, [Basic & Clin Pharm & Tox, 111, 198-205, 2012].

Vortioxetine is typically administered at 1-100 mg/day, such as 1-50 mg/day, such as 5, 10, 15, 20 or 30 mg/day.

Donepezil is typically administered at 1-100 mg/day, such as 1-30 mg/day, such as 1, 5, 15 or 25 mg/day.

That daily dosage of vortioxetine and donepezil may be administered in one portion or in two or more portions.

As demonstrated in the examples part, the combined administration of vortioxetine and donepezil gives rise to a synergistic effect on acetylcholine levels in the brain. Moreover, the examples part also demonstrates that the combined administration of other acetylcholine esterase inhibitors, such as galantamine and rivastigmine does not result in such synergistic effect. The data thus shows that the vortioxetine/donepezil combination is endowed with properties that are unique to this particular combination and not shared by combinations of vortioxetine and other acetylcholine esterase inhibitors.

This finding is further supported by the experiment reported in example 5 where the impact of donepezil and vortioxetine on the memory in rats has been investigated. The test used is the novel object recognition test which is a recognised method to assess the impact of a given treatment on memory. The test relies on the natural propensity of rats to explore novel objects in their environment, and quantifies the extent to which rats remember objects they have already been exposed to. In a habituation phase, rats are allowed to explore the test room environment and two objects which differ in shape, colour and texture. In the test phase, one of the objects is exchanged so that the rats are exposed to one novel object and one familiar object. The time spent exploring the novel and the familiar object is recorded following the administration of test compounds. The results in example 5 show that vortioxetine at 5 mg/kg does not compensate for the memory impairment induced by 0.5 mg/kg scopolamine. Similarly, donepezil at 0.5 mg/kg does not compensate for the memory impairment induced by 0.5 mg/kg scopolamine. Notably, however, vortioxetine and donepezil at these sub-effective dosages when administered together does bring about a significant improvement in the memory of rats. The results from this behavioural model show that the synergistic increase in acetylcholine levels demonstrated in examples 1-4 seem to be reflected in the behaviour of rats.

The receptor occupancy in rats following administration of vortioxetine has been investigated in J pharmacol Exp Ther. 340, 345-366, 2012 and Eur Neuropsychopharm, 23, 133-145, 2013. The results show that vortioxetine dosed at 5-10 mg/kg gives almost full occupancy at relevant targets, such as serotonin transporter, 5-HT$_3$-receptor and 5-HT$_{1B}$-receptor.

The serotonin transporter occupancy in humans was investigated in Basic & Clin Pharmacol &Tox, 110, 401-404, 2012. It was found that 5, 10 and 20 mg/day gives occupancy of 51, 63 and 90%, respectively. The correlation between plasma concentration of donepezil and inhibition of acetylcholine esterase has been investigated in Neurol, 50, 136-145, 1998. It was found that a plasma concentration of ~20 ng/ml gives rise to ~60% inhibition and that a plasma concentration of ~6 ng/ml gives rise to 15% inhibition. In this respect it is also noted that the active sequences of human acetylcholine esterase (Uniprot P22303) and ratus norvegucus (Uniprot P37136) have close to 90% identity. On this background, and mindful of the plasma levels reported in Example 1, it is concluded that the investigated level of vortioxetine (5-10 mg/kg) corresponds to a clinical dose of 5-20 mg vortioxetine per day in humans. Similarly, the investigated dose of donepezil 0.3 mg/kg corresponds to a sub-effective dose, whereas a dose of 1 mg/kg corresponds to a clinical dose of 5-25 mg per day in humans.

The approved maintenance dosage (FDA) for donepezil is 10 or 23 mg per day with 5 mg as initial dose. Thus, in one embodiment, the invention relates to the administration of 1 mg or more, such as 2 mg or more, such as 5 mg or more such as 10 mg or more donepezil per day in combination with vortioxetine, typically administered at 1, 5, 15 or 20 mg per day. Particular examples include 5-10 mg donepezil in combination with 5-20 mg, such as 10 or 15 mg, vortioxetine per day. Particular examples include 10-25 mg donepezil, such as 23 mg donepezil in combination with 5-20 mg, such as 10 or 15 mg, vortioxetine per day.

The active pharmaceutical ingredients used the present invention, i.e. vortioxetine and donepezil may be administered alone as pure compounds or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 21 Edition, Hauber, Ed., Lippincott Williams & Wilkins, 2006.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route may depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound used in the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule, in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing an active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Conveniently, the compounds of the invention are administered in a unit dosage form containing vortioxetine and donepezil each in an amount of about 1-100 mg. In particular, a unit dose of vortioxetine can be 5, 10, 15, 20 or 25 mg. In particular, a unit dose of donepezil can be 1, 2, 5, 10, 15, 20 or 25 mg.

Cognitive dysfunction include a decline in cognitive functions or cognitive domains, e.g. working memory, attention and vigilance, verbal learning and memory, visual learning and memory, reasoning and problem solving e.g. executive function, speed of processing and/or social cognition. In particular, dysfunction may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts. Dementia is a manifestation of cognitive dysfunction. The terms "cognitive deficits" and "cognitive impairment" may be used synonymously with "cognitive dysfunction.

As mentioned above, cognitive dysfunction forms an important part of the clinical manifestation of a number of CNS diseases. For some CNS diseases, cognitive dysfunction is the primary manifestation of the disease, such as e.g. Alzheimer's disease. For other diseases, such as depression, cognitive dysfunction may form part of the clinical manifestation of the diseases, but it is also to a significant extent independent of depression. It has for instance been observed that outcome on cognitive and depression scales do not run in parallel in clinical trials with antidepressants in depressed patients. Often cognitive dysfunction persists upon recovery from depression symptoms. On this background, it is believed that the combined administration of vortioxetine and donepezil is useful for the treatment of dementia in Alzheimer's disease, vascular dementia, dementia in Pick's disease, dementia in Creutzfeldt-Jakob disease, dementia in Huntington's disease, dementia in Parkinson's disease, dementia in HIV (human immunodeficiency virus), dementia in abusers (alcohol or drugs), MCI (mild cognitive impairment), cognitive dysfunction associated with depression and cognitive dysfunction associated with schizophrenia.

In one embodiment, the invention relates to a method for the treatment of a disease selected from cognitive dysfunction; dementia in Alzheimer's disease; vascular dementia; dementia in Pick's disease; dementia in Creutzfeldt-Jakob disease; dementia in Huntington's disease; dementia in Parkinson's disease; dementia in HIV (human immunodeficiency virus); dementia in abusers (alcohol or drugs), MCI (mild cognitive impairment); cognitive dysfunction associated with depression; and cognitive dysfunction associated with schizophrenia, the method comprising the combined administration of a therapeutically effective amount of vortioxetine and donepezil to a patient in need thereof.

In one embodiment, the invention relates to the use of vortioxetine and donepezil for the manufacture of a medicament for the treatment of a disease selected from cognitive dysfunction; dementia in Alzheimer's disease; vascular dementia; dementia in Pick's disease; dementia in Creutzfeldt-Jakob disease; dementia in Huntington's disease; dementia in Parkinson's disease; dementia in HIV (human immunodeficiency virus); dementia in abusers (alcohol or drugs); MCI (mild cognitive impairment); cognitive dysfunction associated with depression; and cognitive dysfunction associated with schizophrenia.

In one embodiment, the invention relates to vortioxetine and donepezil for the combined use in a method for the treatment of a disease selected from cognitive dysfunction; dementia in Alzheimer's disease; vascular dementia; dementia in Pick's disease; dementia in Creutzfeldt-Jakob disease; dementia in Huntington's disease; dementia in Parkinson's disease; dementia in HIV (human immunodeficiency virus); dementia in abusers (alcohol or drugs); MCI (mild cognitive impairment); cognitive dysfunction associated with depression; and cognitive dysfunction associated with schizophrenia.

A "therapeutically effective amount" of compounds as used herein means an amount sufficient to cure, alleviate or partially arrest the clinical manifestations of a given disease and its complications in a therapeutic intervention comprising the administration of said compounds. An amount adequate to accomplish this is defined as "a therapeutically effective amount". Effective amounts for each purpose will depend on the severity of the disease or injury as well as the weight and general state of the subject.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compounds to alleviate the symptoms or complications, to delay the progression of the condition, and/or to cure or eliminate the condition. The patient to be treated is preferably a mammal, in particular a human being.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Amount of a compound administered is indicated as the amount of corresponding free base.

Example 1

Effects of Vortioxetine and Donepezil on Acetylcholine Levels in Hippocampus of Freely-Moving Rats Adult, male, Wistar rats were used for the experiments. The rats were anesthetized before surgery. Each animal was placed in a stereotaxic frame (Kopf Instruments, USA) and an incision was made on the top of the skull. A microdialysis probe with a 4 mm$^2$ exposed surface (polyacrylnitril membrane, Brainlink, the Netherlands) was implanted into the ventral hippocampus. Coordinates were AP=−5.3 mm (to bregma), lateral+4.8 mm (to midline), ventral −8.0 mm (to dura), the incisor bar set at −3.3 mm [Paxinos and Watson, *The rat brain in stereotaxic coordinates*, Academic Press, 6$^{th}$ edition, New York, 2008]. The probes were attached to the skull with stainless steel screws and dental cement. Experiments started after one day of recovery.

Vortioxetine HBr was prepared in 10% 2-hydroxypropyl-β-cyclodextrin at 0, 5 or 10 mg/ml. Donepezil HCl was prepared in ultrapure water at 0, 0.3 or 1.0 mg/ml. Vortioxetine was administered subcutaneously and donepezil was administered intraperitonealy.

At the day of the experiment, the microdialysis probe was connected with flexible PEEK tubing to a microperfusion pump (Harvard) and perfused with artificial cerebrospinal fluid containing 147 mM NaCl, 3.0 mM KCl, 1.2 mM CaCl$_2$ and 1.2 mM MgCl$_2$ at a flow rate of 1.5 µl/min. After two hours of prestabilisation, samples (30 µl) were collected and stored in 20 mM formic acid and 0.04% ascorbic acid (10 µl).

The concentration of acetylcholine in the samples was determined by HLPC fitted with tandem mass spectroscopy (MS/MS) for detection using acetyl-β-methyl-choline as internal standard. Chromatographic separation was performed on a reversed phase Phenomenex Synergi Max-RP column (2.0×150 mm, particle size 4 µm) at 50° C. Components were separated using an isocratic flow of eluent A (20 mM ammonium acetate, 5% acetonitril and 0.3% trifluoroacetic acid) at a flow rate of 0.25 ml/min.

MS analyses were performed using an API 3000 MS/MS system consisting of an API 3000 MS/MS detector and a Turbo Ion Spray interface. The acquisitions were performed in positive ionisation mode with ionisation spray voltage set at 4.5 kV and a probe temperature at 550° C. The instrument was operated in multiple-reaction-monitoring mode.

The average of three pre-administration samples was set to 100%. If relative samples were <50% or >150% they were considered outliers and not used for baseline calculation. All post-administration samples were expressed as a percentage of basal level within the same subject. Time and treatment effects were compared using two-way ANOVA for repeated measurements followed by Student-Newman-Keuls post-hoc test. Significance was defined as $p<0.05$ Groups of five animals were exposed to combinations of vortioxetine (vehicle, 5 mg/kg and 10 mg/kg sc) and donepezil (vehicle, 0.3 mg/g and 1 mg/kg ip) administered simultaneously. The data is depicted in FIG. 1*a-c* and 2*a-b*.

In addition, blood samples were taken from each animal to measure the plasma level of the active ingredients. The table 1 below depicts the results

TABLE 1

|  | Vortioxetine | | | | | |
|  | Vehicle | | 5 mg/kg | | 10 mg/kg | |
| Donepezil | Vortioxetine in plasma (ng/ml) | Donepezil in plasma (ng/ml) | Vortioxetine in plasma (ng/ml) | Donepezil in plasma (ng/ml) | Vortioxetine in plasma (ng/ml) | Donepezil in plasma (ng/ml) |
| Vehicle | 0 | 0 | ND | ND | ND | ND |
| 0.3 mg/kg | 0 | 6.4 | 149 | 7.8 | 317 | 6.4 |
| 1 mg/kg | 0 | 21 | 137 | 28 | 317 | 26 |

The data in the above table shows that the animals were, indeed, exposed to the two active ingredients, and that consistent levels were found throughout the experiments The data obtained for the acetylcholine levels in ventral hippocampus and depicted in FIGS. 1*a-c* and 2*a-b* shows that acetylcholine levels at 10 mg/kg vortioxetine and 1 mg/kg donepezil were significantly increased compared to acetylcholine levels at any other treatment. The data also shows that acetylcholine levels at 5 mg/kg vortioxetine and 1 mg/kg donepezil were significantly increased compared to acetylcholine levels at any level of vortioxetine at 0 and 0.3 mg/kg donepezil. The data also shows that the administration of donepezil at 1 mg/kg and vehicle significantly increased acetylcholine levels compared to vehicle+vehicle treatment.

Example 2

Effect of Vortioxetine on Acetylcholine Levels in Hippocampus of Freely-Moving Rats This experiment was carried out essentially as described in Example 1. The analytical set-up was slightly modified as follows. Chromatographic separation was performed on a reverse-phase 150×2.00 mm (4 µm) analytical column (Phenomenex Synergy MAX-RP, Bester) protected by a 4×2.0 mm guard column (Phenomenex Synergy MAX-RP AJO-6073, Bester), both held at a temperature of 30° C. The mobile phase (isocratic) consisted of water acetonitrile (ACN), and trifluoroacetic (TFA) acid (water:ACN:TFA=95.0:5:0.1 v/v/v %) at a flow rate of 0.200 ml/min.

MS analyses were performed using a API 3000 MS/MS system consisting of a API 3000 MS/MS detector and a Turbo Ion Spray interface (both from Applied Biosystems, the Netherlands). The acquisitions were performed in positive ionization mode with ion spray voltage set at 5.5 kV, with a probe temperature of 450° C.

Groups of five animals were exposed vortioxetine (vehicle, 2.5 mg/kg, 5 mg/kg and 10 mg/kg sc). The data are depicted in FIG. 3.

The results obtained in Examples 1 and 2 clearly establish that the extra-cellular acetylcholine levels obtained as a result of the combined administration of vortioxetine and donepezil are significantly higher than the levels obtained upon individual administration of vortioxetine and donepezil. That is, a synergistic effect on acetylcholine levels between vortioxetine and donepezil has been demonstrated.

A synergistic effect between two pharmaceutically active compounds may be exploited in at least two ways. The doses normally applied in mono-treatment using the two pharmaceutically active compounds can be maintained in a combination treatment and a larger than expected clinical effect can be achieved. Alternatively, lower doses than normally applied in mono-treatment using the two pharmaceutically active compounds can be applied for either or both of the compounds in order to maintain the clinical effect, however at a lower drug exposure. A lower drug exposure may be beneficial because adverse events can be expected to increase with increasing drug loads.

Example 3

Effects of Vortioxetine and Galantamine on Acetylcholine Levels in Hippocampus of Freely Moving Rats Adult, male Sprague Dawley rats were used in the experiments. The rats were anesthetized before surgery. The animals were placed in a stereotaxic frame (Kopf instruments, USA), and CMA12 guide cannulas (CMA Microdialysis, Sweden) were implanted aiming into the ventral hippocampus. Coordinates for the tips of the probes were AP=−5.3 mm to bregma, lateral (ML)=−4.8 mm to midline and ventral=−8.0 mm to dura (Paxinos and Watson).

Galanthamine, the chemical name of which is (4aS,6R,8aS)-4a,5,9,10,11,12-hexahydro-3-methoxy-11-methyl-6H-benzofuro[3a,3,2-ef][2]benzazepin-6-ol, was administered as the HBr salt. Vortioxetine was administered as the HBr salt. Vortioxetine and galantamine were prepared in 0.9% saline. Vortioxetine was administered subcutaneously at 10 mg/kg and galantamine was administered subcutaneously at 0.3 mg/kg and 1.0 mg/kg.

The day before the experiment, a microdialysis probe (CMA/12, 4 mm, PAES, MWKO 100 kDa) was inserted into the respective guide cannula in the awake rats. The probes were perfused at a constant flow-rate of 1 µl/min with sterile artificial cerebrospinal fluid containing 148 mM NaCl, 4 mM KCl, 0.8 mM MgCl2, 1.4 mM CaCl2, 1.2 mM Na2HPO4, 0.3 mM NaH2PO4, pH 7.2. At the day of the experiment, samples were collected in 30 min intervals prior to administration to define the baseline. The data is presented as percentage of baseline within the same animal. Significance is defined as $p < 0.05$. Animals received treatments according to experimental protocol and samples were collected at 30 minutes intervals.

The concentration of acetylcholine in the samples was determined using a Waters Acquity HPLC system equipped with a Sunshell RP-Aqua 2.1×100 mm, 2.6 um particle column fitted with a Waters Quattro Premier XE triple quadrupole mass spectrometer operating in the MS/MS mode. Components were separated using an isocratic flow of eluent A (100 mM ammonium acetate in milliQ water).

Groups of 6-8 animals were exposed to combinations of vortioxetine (vehicle and 10 mg/kg) and galantamine (vehicle, 0.3 mg/kg and 1.0 mg/kg). Injection of galantamine was 60 minutes prior to the injection of vortioxetine. The data obtained is depicted in FIG. 4a-4c The data show that the administration of galantamine at 0.3 and 1.0 mg/kg gives rise to a dose dependent, significant increase in acetylcholine levels in hippocampus of freely moving rats. The results also shows that administration of vortioxetine at 10 mg/kg gives rise to a significant increase in the acetylcholine levels in hippocampus of freely moving rats. These results support the findings in example 2. The data also shows that administration of galantamine at 0.3 or 1.0 mg/kg in combination with vortioxetine does not give rise to a significant increase in the acetyl choline levels compared to administration of galantamine at any level together with vehicle. In fact, the numerical values of acetylcholine levels are lower for the combined administration of galantamine at any level and vortioxetine compared to the administration of galantamine at any level and vehicle. Importantly, the results from example 3 show that the combined administration of vortioxetine and galantamine does not have a synergistic effect on acetylcholine levels.

Example 4

Effects of Vortioxetine and Rivastigmine on Acetylcholine Levels in Hippocampus of Freely Moving Rats Example 4 was carried essentially similar to example 3 except for the test compounds. Rivastigmine was prepared in 0.9% saline and administered subcutaneously at 0.2 mg/kg and 0.6 mg/kg. Rivastigmine, the chemical name of which is (S)—N-ethyl-N-methyl-3-[1-(dimethylamino)ethyl]-phenyl carbamate, was administered as the tartrate salt.

The data obtained are depicted in FIG. 5a-5b and FIG. 4a for the vehicle-vehicle tests.

The data shows that administration of rivastigmine at 0.2 and 0.6 mg/kg dose-dependently and significantly increases acetylcholine levels. The data also show that the combined administration of vortioxetine and rivastigmine at 0.6 mg/kg does not give rise to an increase in the acetylcholine levels compared to the administration of rivastigmine and vehicle. The data show that the combined administration of rivastigmine at 0.2 mg/kg and vortioxetine gives rise to a significantly higher level of acetylcholine compared to the administration of rivastigmine at 0.2 mg/kg and vehicle. The data shows that the sum of the acetylcholine levels following administration of vortioxetine+vehicle and rivastigmine at 0.2 mg/kg+vehicle is not different from the acetylcholine levels following the combined administration of rivastigmine at 0.2 mg/kg and vortioxetine. This shows that the combined administration of vortioxetine and rivastigmine at 0.2 mg/kg gives rise to an additive effect on the acetylcholine levels in the hippocampus of freely moving rats. Importantly, the data shows that the combined administration of rivastigmine and vortioxetine does not give rise to a synergistic effect on the acetylcholine levels in hippocampus.

Example 5

Effects of Donepezil and Vortioxetine on Short-Term Episodic Memory in Rats

The novel object recognition task (NOR) was used to assess the impact of vortioxetine and donepezil, alone or in combination, on the memory of rats with scopolamine-induced memory impairment. Sprague-Dawley rats were used One day 1 and day 2 of the experiment the rats received two habituation sessions to the test room environment including two objects (familiar objects). Each session lasted 6 minutes. Rats that did not explore the objects or rats that had a natural preference for one object over the other were excluded from the trial. At the test day, five groups of rats received a third habituation test (familiarization trial) after which they were removed from the test apparatus and one of the objects was replaced with a novel object. Four hours later, the rats were put back in the test apparatus (test phase) and the time used exploring of the familiar and the novel object was recorded.

The five groups of rats were treated with vehicle, scopolamine, vortioxetine, donepezil and vortioxetine+donepezil intraperitonelt as follows. The numbers in parenthesis indicate the number of rats in each group

|  | 1 (13) | 2 (8) | 3 (8) | 4 (4) | 5 (6) |
|---|---|---|---|---|---|
| Saline 40 minutes prior to familiarization trial | x |  |  |  |  |
| Scopolamine (0.5 mg/kg) 40 minutes prior to familiarization trial |  | x | x | X | x |
| Donepezil at 0.5 mg/kg 20 minutes prior to familiarization trial |  |  |  | x |  |
| Vortioxetine at 5 mg/kg 20 minutes prior to familiarization trial |  |  | X |  |  |
| Donepezil at 0.5 mg/kg and vortioxetine at 5 mg/kg 20 minutes prior to familiarization trial |  |  |  |  | x |

FIG. 6 depicts the exploration of the novel object by means of the recognition index (RI) defined as $$RI = \frac{N-F}{N+F} \times 100\%$$

wherein N is time spent with novel object and F is time spent with familiar object.

The data show that RI for groups 2, 3 and 4 is significantly ($p<0.001$) lower than RI for group 1, and that RI for group 5 is significantly ($p<0.05$) higher than RI for any of groups 2, 3 and 4. This shows scopolamine impairs short-term memory in rats and that neither vortioxetine at 5 mg/kg nor donepezil at 0.5 mg/kg is able to reverse this impairment. In contrast hereto, the combined effect of vortioxetine at 5 mg/kg and donepezil at 0.5 mg/kg does reverse the memory impairment induced by scopolamine.

The invention claimed is:

1. A pharmaceutical composition, comprising vortioxetine and donepezil together with a pharmaceutically acceptable excipient.

2. The composition according to claim 1, wherein the composition comprises 5-25 mg donepezil.

3. The composition according to claim 1, wherein the composition comprises 5-20 mg vortioxetine.

4. A method for the treatment of a disease selected from the group consisting of cognitive dysfunction; dementia in Alzheimer's disease; vascular dementia; dementia in Pick's disease; dementia in Creutzfeldt-Jakob disease; dementia in Huntington's disease; dementia in Parkinson's disease; dementia in HIV (human immunodeficiency virus) infection; dementia in abusers (alcohol or drugs); MCI (mild cognitive impairment); cognitive dysfunction associated with depression; and cognitive dysfunction associated with schizophrenia, the method comprising the combined administration of vortioxetine and donepezil to a patient in need thereof.

5. The method according to claim 4, wherein said patient is administered 5-25 mg donepezil.

6. The method according to claim 4, wherein said patient is administered 5-20 mg vortioxetine.

7. The method according to claim 5, wherein said patient is administered 5-20 mg vortioxetine.

8. The composition according to claim 2, wherein the composition comprises 5-20 mg vortioxetine.

* * * * *